US012521284B1

(12) United States Patent
Alston, Sr.

(10) Patent No.: US 12,521,284 B1
(45) Date of Patent: Jan. 13, 2026

(54) URINE ABSORBING SHEATH FOR MEN

(71) Applicant: Stephen Alston, Sr., Glenarden, MD (US)

(72) Inventor: Stephen Alston, Sr., Glenarden, MD (US)

( * ) Notice: Subject to any disclaimer, the term of this patent is extended or adjusted under 35 U.S.C. 154(b) by 335 days.

(21) Appl. No.: 18/216,483

(22) Filed: Jun. 29, 2023

(51) Int. Cl.

| | |
|---|---|
| ***A61F 13/471*** | (2006.01) |
| ***A61F 5/44*** | (2006.01) |
| ***A61F 5/443*** | (2006.01) |
| *A61F 13/15* | (2006.01) |

(52) U.S. Cl.
CPC .......... *A61F 13/471* (2013.01); *A61F 5/4401* (2013.01); *A61F 5/4408* (2013.01); *A61F 5/443* (2013.01); *A61F 2013/15121* (2013.01)

(58) Field of Classification Search
CPC .... A61F 13/471; A61F 5/4401; A61F 5/4408; A61F 5/443; A61F 2013/15121
See application file for complete search history.

(56) References Cited

U.S. PATENT DOCUMENTS

| | | | | |
|---|---|---|---|---|
| 5,013,308 A * | 5/1991 | Sullivan | A61F 5/453 | 604/351 |
| 6,479,726 B1 * | 11/2002 | Cole | A61F 13/471 | 604/350 |
| D613,855 S * | 4/2010 | Pena | D24/124 | |
| 8,961,482 B2 * | 2/2015 | Heyman | A61F 5/451 | 604/352 |
| 9,028,460 B2 * | 5/2015 | Medeiros | A61F 5/451 | 604/347 |
| 9,713,547 B2 | 7/2017 | Lee | | |
| 10,307,306 B2 * | 6/2019 | Henderson | A61F 13/5611 | |
| 10,722,406 B1 * | 7/2020 | Baraka | A61F 13/539 | |
| 12,257,173 B2 * | 3/2025 | Newton | A61F 5/445 | |
| 2002/0026163 A1 * | 2/2002 | Grundke | A61F 5/453 | 604/347 |
| 2008/0071237 A1 * | 3/2008 | Chen | A61F 13/515 | 604/385.05 |
| 2009/0270822 A1 * | 10/2009 | Medeiros | A61F 5/451 | 604/347 |
| 2019/0091075 A1 | 3/2019 | Jones, Jr. | | |
| 2023/0020563 A1 * | 1/2023 | Sharma | A61F 5/443 | |
| 2023/0240884 A1 * | 8/2023 | Davis | A61F 5/441 | 604/349 |
| 2024/0065874 A1 * | 2/2024 | Schneider | A61F 5/4401 | |
| 2024/0115412 A1 * | 4/2024 | Meroi | A61F 5/4401 | |

* cited by examiner

*Primary Examiner* — Guy K Townsend
(74) *Attorney, Agent, or Firm* — Sanchelima & Associates, P.A.; Jesus Sanchelima; Christian Sanchelima

(57) ABSTRACT

An urine absorbing sheath for men including a sheath assembly and an attaching assembly. The sheath assembly includes sheath. The sheath is hollow and has an open top portion. The sheath is absorbent and includes an absorbent pad on a bottom rear portion thereof. The sheath is used to cover an user's penis. The attaching assembly includes at least one attaching member having adhesive means. The at least one attaching member is used to adhere the sheath to the user's penis in a predetermined position. The sheath absorbs sweat, urine and any other liquids.

10 Claims, 2 Drawing Sheets

URINE ABSORBING SHEATH FOR MEN

BACKGROUND OF THE INVENTION

1. Field of the Invention

The present invention relates to a urine absorbing sheath for men and, more particularly, to an urine absorbing sheath for men that allows to absorb urine from penis while separating the penis from the testicles.

2. Description of the Related Art

Several designs for absorbing pads have been designed in the past. None of them, however, include a sheath capable of being removable attached covering the pennis so the sheath can absorb urine.

Applicant believes that a related reference corresponds to U.S. Pat. No. 9,713,547 issued for a fluid capturing device that is configured to encircle a penis and capture urine or other secretions. Applicant believes that another related reference corresponds to U.S. patent application No. 2019/0091075 issued for a male incontinence device in the form of a water-proof sleeve with an absorbent inner layer which is configured to receive a penis. None of these references, however, teach of an absorbing sheath for men that is comprised of a pennis worn sheath with an adhesive layer which removable secures the sheath to the penis, the sheath also contains an inner urine absorbing layer, a rubber or plastic guiding member, and an external absorbent pad which is configured to be placed between the penis and the testicles.

Other documents describing the closest subject matter provide for a number of more or less complicated features that fail to solve the problem in an efficient and economical way. None of these patents suggest the novel features of the present invention.

SUMMARY OF THE INVENTION

It is one of the objects of the present invention to provide an urine absorbing sheath for men that is portable and removable so a person can remove the sheath without need of taking the pants off.

It is another object of this invention to provide an urine absorbing sheath for men that includes an adhesive layer so the sheath can adhere to the underwear preventing the sheath from moving.

It is still another object of the present invention to provide a urine absorbing sheath for men that includes straps which help to keep the sheath in place covering the pennis.

It is yet another object of this invention to provide such a device that is inexpensive to implement and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE EMBODIMENTS OF THE INVENTION

Figure 1:
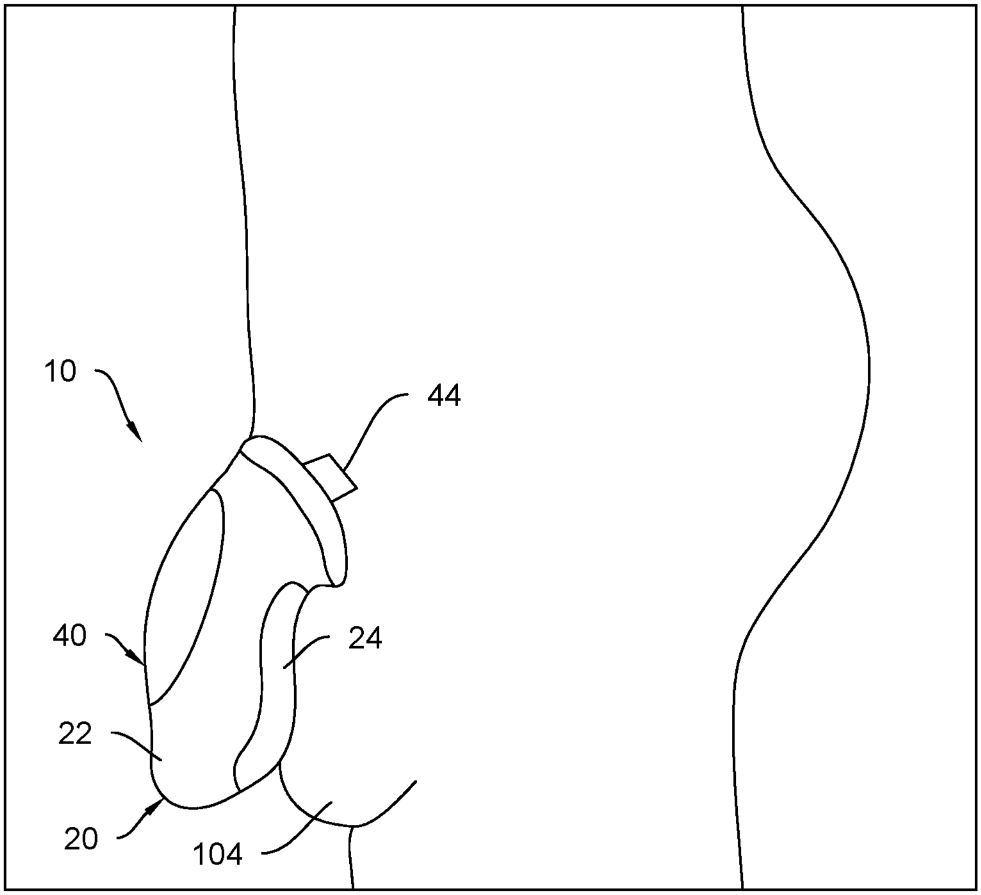
FIG. 1 represents a side operational view of the present invention 10.

Referring now to the drawings, where the present invention is generally referred to with numeral 10, it can be observed that it basically includes a sheath assembly 20 and an attaching assembly 40. It should be understood there are modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

The sheath assembly 20 may include a sheath 22, a pad 24, an elastic liner 26, and an absorbent layer 27. As best illustrated in FIG. 1 the sheath 22 may substantially have a cylindrical shape with an open top end. It also may be suitable for the sheath 22 to have a rectangular shape, a triangular shape, or any other suitable shape. In a preferred embodiment the sheath 22 may have such a shape that fits covering in abutting contact a user's penis. The sheath 22 may be made of polyurethane, cotton, leather, or any other suitable material. In a preferred embodiment the sheath 22 may be made of a waterproof material. The sheath 22 may have the absorbent layer 27 entirely extending about an inner surface thereof. The absorbent layer 27 may absorb urine or any other liquid while the sheath 22 may prevent the liquid to go out therefrom. The absorbent layer 27 may be made of cellulose, fleece or any other suitable material enclosing sodium polyacrylate or any other absorbent material.

The open top portion of the sheath 22 may include the elastic liner 26 extending about a perimeter thereof. The elastic liner 26 may be made of a fabric material enclosing an elastic fabric. User's penis may be introduced through the open top portion of the sheath 22.

The pad 24 may be located on a rear side of the sheath 22. The pad 24 may be made of a fabric material included but not limited to cotton and fleece enclosing an absorbent pad made of polypropylene, cellulose, and so on. The pad 24 may absorb sweat. The pad 24 may be integrally formed in the sheath 22.

Figure 3:
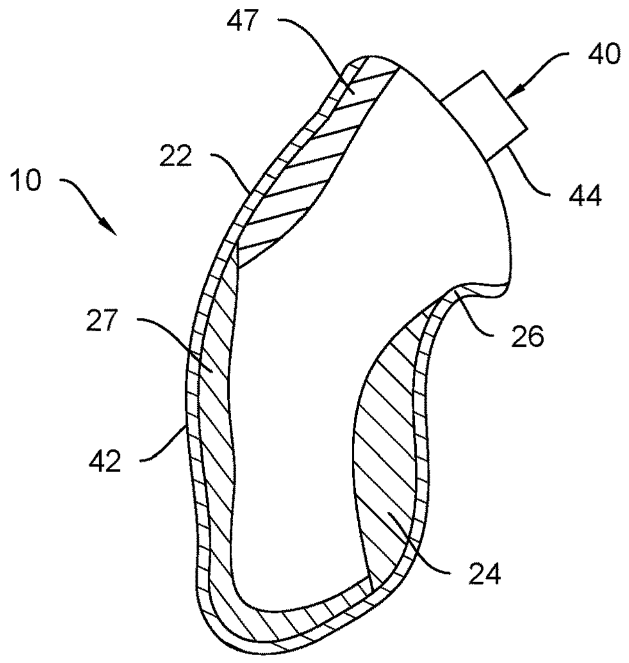
FIG. 3 illustrates a cross sectional side view of the present invention 10. The present invention 10 includes a sheath assembly 20 and an attaching assembly 40.

Referring now to FIG. 3 it can be observed that the attaching assembly 40 may include an adhesive portion 42, a rubber portion 47 and attaching members 44. The adhesive portion 42 may extend about a length of a front portion of the sheath 22. The adhesive portion 42 may include neoprene, nitrile rubber, butadiene rubber impregnated in the sheath 22. In another embodiment the adhesive portion 42 may be adhered to the sheath 22. The adhesive portion 42 may be used to adhere the sheath 22 to the user's penis.

The rubber portion 47 may be located within the sheath 22. In a preferred embodiment the rubber portion 47 may be located on a front inner portion of the sheath 22. The rubber portion 47 may be made of butyl rubber, silicone rubber, neoprene, silicone rubber, or any other suitable material. The rubber portion 47 may allow the user's penis to move through the sheath 22. In one embodiment the rubber portion 47 may be lubricated. The rubber portion 47 may also prevent the movement of the sheath 22 when adhered to the user's penis.

Figure 2:
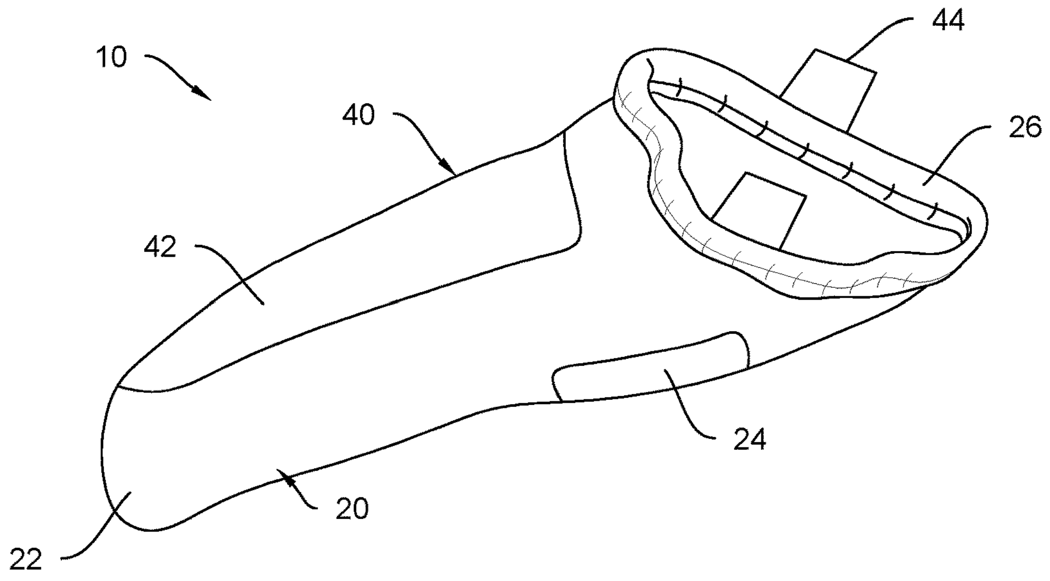
FIG. 2 shows an isometric view of the present invention 10.

In a preferred embodiment the attaching members 44 may protrude outwardly and upright from a top portion of the sheath 22, as best shown in FIG. 2. It also may be suitable for the attaching members 44 to protrude from a rear side, the front side, the left side, or from any other portion of the sheath 22. The attaching members 44 may be made of polyurethane, polyvinyl chloride, cotton, or any other suitable material. The attaching members 44 may include a posterior side and an anterior side. The anterior side of the attaching members 44 may include adhesive materials impregnated therein. It should be understood that the adhesive portion 42 and the anterior side of the attaching members 44 may be covered with a plastic covering prior to use.

In a preferred embodiment the present invention 10 may be worn covering the user's penis to absorb urine therefrom and sweat from genital area. In a preferred embodiment the present invention 10 may be held in place by means of attaching members 44, adhesive portion 42 and the rubber portion 47 in such a manner that the present invention 10 is adapted to be worn and removed without the need of removing jeans, pants or the underwear.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. An urine absorbing sheath for men, comprising:

a sheath assembly, wherein said sheath assembly includes a sheath, the sheath has an open top portion, the sheath includes an absorbent layer therein, the sheath includes an absorbing pad on a bottom portion thereof, wherein said absorbing pad is configured to be positioned between a penis and testicles during use, the sheath is configured to be worn enclosing a penis; and an attaching assembly, wherein said attaching assembly includes at least one attaching member, said at least one attaching member protrudes from a top end of said sheath, said at least one attaching member is configured to adhere the sheath in a predetermined position, wherein said sheath has a curved anatomical shape with a front portion and a rear portion, said front portion being convex and said rear portion having a concave curvature as shown; wherein said sheath is adapted to be worn and removed without removing pants or underwear; wherein said sheath has a layered interior structure comprising said rubber portion in abutting contact with said absorbent layer, and said absorbent layer in abutting contact with said pad.

2. The urine absorbing sheath for men set forth in claim 1, wherein said open top portion includes an elastic liner extending about a periphery thereof, wherein said elastic liner is positioned at a proximal end of said sheath adjacent said open top portion.

3. The urine absorbing sheath for men set forth in claim 1, wherein said attaching assembly includes an adhesive portion, said adhesive portion extends about a length of an exterior surface of said sheath, wherein said adhesive portion extends longitudinally along a front exterior surface of said sheath between said open top portion and said bottom portion, and wherein said adhesive portion is covered with a protective plastic covering prior to us.

4. The urine absorbing sheath for men set forth in claim 1, wherein said sheath includes a rubber portion, said rubber portion is located on a front interior portion of the sheath, wherein said rubber portion is configured to allow movement of the penis through the sheath while preventing movement of the sheath when adhered to the penis.

5. The urine absorbing sheath for men set forth in claim 3, wherein said adhesive portion and said at least one attaching member are impregnated with an adhesive material.

6. The urine absorbing sheath for men set forth in claim 1, wherein said sheath has a cylindrical silo shape with an anatomical curvature conforming to a natural penis shape.

7. The urine absorbing sheath for men set forth in claim 1, wherein said at least one attaching member includes a first attaching member and a second attaching member having a rectangular flared shape with adhesive means on the anterior sides thereof, wherein said first and second attaching members protrude upwardly and outwardly from said open top portion.

8. The urine absorbing sheath for men set forth in claim 1, wherein an exterior portion of said sheath is made of a waterproof material, and wherein said absorbent layer is entirely disposed within an inner surface of said sheath.

9. An urine absorbing sheath for men, comprising:

a sheath assembly, wherein said sheath assembly includes a sheath, the sheath has an open top portion, the sheath includes an absorbent layer therein and a waterproof layer on an exterior surface thereof, the sheath includes an absorbing pad on a rear exterior portion thereof, wherein said absorbing pad is configured to be positioned between a penis and testicles during use, the sheath is configured to be worn enclosing a penis, the sheath has a cylindrical silo shape with a curved anatomical configuration, the open top portion is delimited by an elastic liner, the elastic liner extends about a perimeter of said open top portion, the sheath is hollow; and an attaching assembly, wherein said attaching assembly includes at least one attaching member, said at least one attaching member protrudes from a top end of said sheath, said at least one attaching member is configured to adhere the sheath in a predetermined position; wherein, within an interior cross-section of said sheath, said rubber portion abuts an inner surface of said absorbent layer at a first interior location, and said absorbent layer abuts said pad at a second interior location.

10. An urine absorbing sheath for men, consisting of:

a sheath assembly, wherein said sheath assembly includes a sheath, the sheath has an open top portion, the sheath includes an absorbent layer therein and a waterproof layer on an exterior surface thereof, the sheath includes an absorbing pad on a rear exterior portion thereof, the sheath is configured to be worn enclosing a penis, the sheath has a cylindrical silo shape, the open top portion is delimited by an elastic liner, the elastic liner extends about a perimeter of said open top portion, the sheath is hollow; and an attaching assembly, wherein said attaching assembly includes at least one attaching member, and adhesive portion and a rubber portion, said at least one attaching member protrudes from a top end of said sheath, said at least one attaching member includes a first attaching member and a second attaching member having a rectangular flared shape with adhesive means on the anterior sides thereof protruding upwardly from said open top portion, said at least one attaching member is configured to adhere the sheath in a predetermined position, wherein said adhesive portion extends about a length of a front exterior side of the sheath, wherein said adhesive portion includes adhesive materials impregnated therein, wherein said rubber portion is located on a front interior portion of the sheath, the rubber portion is made of a rubber material, wherein said absorbing pad is configured to be positioned between the penis and testicles during use; wherein said rubber portion is positioned adjacent to and in abutting contact with said absorbent layer at a front interior portion of said sheath; wherein said absorbent layer is positioned adjacent to and in abutting contact with said pad at a rear interior portion of said sheath.

* * * * *